United States Patent [19]

Suptitz

[11] Plant 4,641

[45] Feb. 3, 1981

[54] POINSETTIA PLANT

[75] Inventor: Dieter Suptitz, Hamburg, Fed. Rep. of Germany

[73] Assignee: Paul Ecke, Jr., Encinitas, Calif.

[21] Appl. No.: 42,858

[22] Filed: May 29, 1979

[30] Foreign Application Priority Data

Jun. 27, 1975 [DE] Fed. Rep. of Germany ..... 11/75

[51] Int. Cl.[3] ..... A01H 5/00

[52] U.S. Cl. ..... Plt./86

[58] Field of Search ..... Plt./86

[56] References Cited

U.S. PATENT DOCUMENTS

P.P. 3,764 8/1975 Hegg ..... Plt./86

*Primary Examiner*—Robert E. Bagwill

*Attorney, Agent, or Firm*—Charles W. Rummler

[57] ABSTRACT

A new and distinct poinsettia cultivar originating as a sport of the Hegg variety disclosed in U.S. Plant Pat. No. 2,962 and distinguished by the bright red color of its relatively large bracts which have stronger stems and by its early blooming characteristic, especially when grown in the northern latitudes under the poor growing conditions of reduced light intensity and duration. This plant is medium to short in height, compared to currently produced varieties, is self-branching with many side shoots whether pinched or unpinched, and its rooting habit is uniform and fast. When grown for blooming at the same time as most other Hegg varieties, this plant may be grown at a lower temperature than usually required.

1 Drawing Figure

BACKGROUND OF THE NEW PLANT

This new poinsettia cultivar originated as a sport of one of many plants of the parent stock being grown in my greenhouse at Hamburg, Germany, and was discovered by me as the individual plants were approaching maturity, the brighter red color of this sport standing out from the others in the field so as to be immediately noticeable. This distinctive and attractive characteristic of the sport prompted me to propagate it in my greenhouse by means of vegetative cuttings and asexual reproduction of the new variety through many generations at Hamburg, Germany, and at Encinitas, Calif., as demonstrated that its novel characteristics hold true from generation to generation and appear to be firmly fixed.

DESCRIPTION OF THE DRAWINGS

My new poinsettia variety is illustrated by the accompanying full color photographic drawing, in which the upper view shows a full face view of the mature plant and the lower view shows the form and foliage of a mature potted plant, the color rendition being as nearly true as it is reasonably possible to obtain by conventional photographic procedures.

DESCRIPTION OF THE NEW PLANT

The following is a detailed description of my new poinsettia cultivar with color designations according to the R.H.S. Colour Chart published by The Royal Horticultural Society of London, England.

THE PLANT

Origin: Sport.

Parentage: A Hegg variety as disclosed by U.S. Plant Pat. No. 2,962.

Classification:

*Botanic.*—*Euphorbia pulcherrima.*

*Commercial.*—Greenhouse poinsettia.

Form: Shrub.

Height: Medium to short, somewhat less in height than that of currently produced commercial varieties.

Growth habit: Upright and vigorous, with self-branching side shoots, when grown as a single stem; may require a growth regulator.

*As a branched plant.*—Upright with many stems producing a bushy, full appearance.

Growth rate: Very fast; rooting occurs in 10 to 15 days under automatic mist and the plant will bloom in about 8 weeks at a night temperature of 15° to 17° during October and November; under poor light conditions, a somewhat higher temperature may be needed.

Blooming habit: This variety blooms approximately 7 days earlier than Annette Hegg "Supreme" (U.S. Plant Pat. No. 3,392) when grown in the northern latitudes under the typically poor conditions of reduced light intensity and duration. When bloomed at the same time as most other Annette Hegg varieties, an energy saving lower temperature may be used.

Foliage: Type — Alternate and horizontal with medium persistence and normal abundance.

*Leaf size.*—Medium, about 4 to 5 inches long and about 2½ to 4 inches wide.

*Leaf shape.*—Substantially ovate, also bi-lobed and undulated, some with acuminate tip.

*Aspect.*—Upper side — Dull with indented vein. Under side — Dull with ordinary veining.

*Color.*—Upper side — Dark Green 139A/147A. Under side — Dark Green 137C/147B.

*Retention.*—Foliage lasts very well as with the Annette Hegg varieties in general.

*Bracts.*—Number — Generally 10 to 15. Size: Various, up to 7 inches long and about 4 inches wide. Shape: Obovate to elliptic, often undulated and acuminate. Petioles: Medium and strong from about ¾ inch to about 2 inches long. Color: Bright Red. Upper side — 45A/46B. Under side — 45D/47B. Retention: Persistence is medium and similar to the U.S. Plant Pat. No. 2,962 variety.

This new poinsettia cultivar while having the good features of its parent, also has bracts of a brighter red color much like the Annette Hegg varety "Supreme" (U.S. Plant Pat. No. 3,392) which fades very little when mature. The color, while close to other poinsettia varieties, is unique in its precise shade. This is especially true when this new plant is grown in northern latitudes where daylight is limited. This plant blooms approximately 7 days earlier than "Supreme" and its bracts average a larger size with stronger stems which have less tendency for breakage.

I claim:

1. A new and distinctive variety of red poinsettia substantially as herein shown and described, characterized by the striking red color of its larger than average bracts, its early blooming habit, its medium to short height, its vigorous upright growth habit, and its uniform and fast rooting habit.

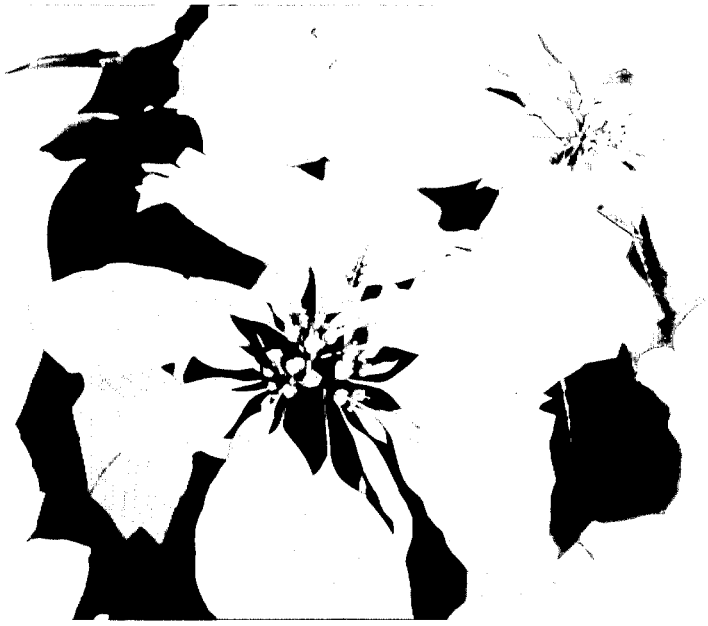
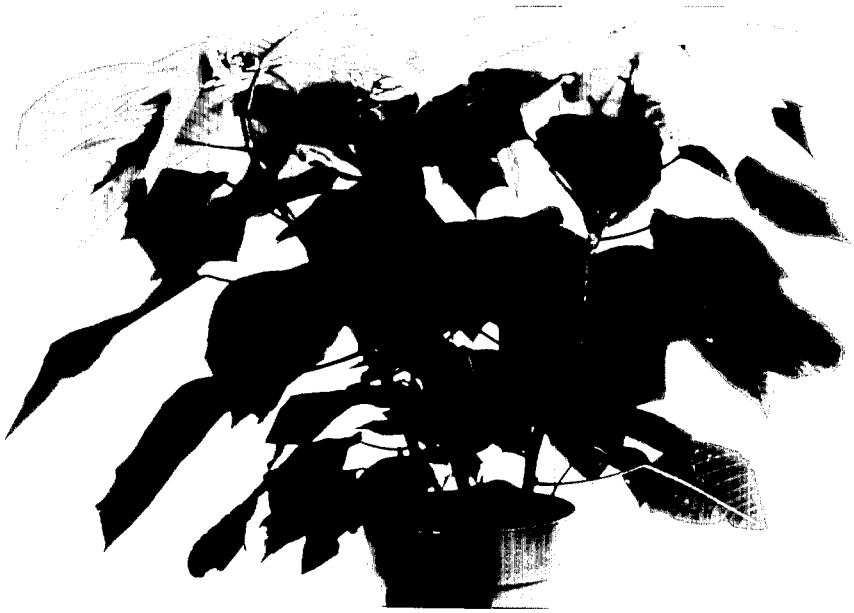

* * * * *